United States Patent
Smith et al.

(10) Patent No.: US 12,364,395 B2
(45) Date of Patent: Jul. 22, 2025

(54) DUAL BRILLOUIN-PHOTOACOUSTIC MICROSCOPY

(71) Applicant: Arizona Board of Regents, Scottsdale, AZ (US)

(72) Inventors: Barbara Smith, Tempe, AZ (US); Christopher Miranda, Mesa, AZ (US)

(73) Assignee: Arizona Board of Regents on behalf of Arizona State University, Scottsdale, AZ (US)

(*) Notice: Subject to any disclaimer, the term of this patent is extended or adjusted under 35 U.S.C. 154(b) by 115 days.

(21) Appl. No.: 17/533,270

(22) Filed: Nov. 23, 2021

(65) Prior Publication Data
US 2022/0160236 A1    May 26, 2022

Related U.S. Application Data

(60) Provisional application No. 63/117,002, filed on Nov. 23, 2020.

(51) Int. Cl.
*A61B 5/00*    (2006.01)
*A61B 3/103*    (2006.01)

(52) U.S. Cl.
CPC ............ *A61B 5/0095* (2013.01); *A61B 3/103* (2013.01)

(58) Field of Classification Search
CPC ....... A61B 5/0095; A61B 3/103; A61B 5/742; A61B 5/0075
See application file for complete search history.

(56) References Cited

U.S. PATENT DOCUMENTS

| | | |
|---|---|---|
| 2,761,077 A | 8/1956 | Harris |
| 5,769,086 A | 6/1998 | Ritchart |
| 5,916,210 A | 6/1999 | Winston |
| 9,594,075 B2 | 3/2017 | Eggan |

(Continued)

FOREIGN PATENT DOCUMENTS

| | | |
|---|---|---|
| DE | 102015114670 | 3/2017 |
| EP | 3118608 | 1/2017 |
| WO | 9903399 A1 | 1/1999 |

OTHER PUBLICATIONS

Yao, Da-Kang et al. "Photoacoustic measurement of the Grüneisen parameter of tissue." Journal of biomedical optics vol. 19,1 (2014): 17007. doi:10.1117/1.JBO.19.1.017007 (Year: 2014).*

(Continued)

*Primary Examiner* — Sean D Mattson
*Assistant Examiner* — Michael Yiming Fang
(74) *Attorney, Agent, or Firm* — Riverside Law LLP

(57) ABSTRACT

A system for calculating a Grüneisen parameter of a target tissue is disclosed. The system comprises a first light source configured to emit a first light signal to the target tissue, thereby generating an acoustic signal in the target tissue. The system further comprises a second light source configured to emit a second light signal to the target tissue, which interacts with the acoustic signal, (e.g., in the manner of Brillouin scattering) to generate a backscattered light signal. The system further comprise a light sensor configured to detect the backscattered light signal and a processor configured to receive the backscattered light signal from the light sensor and calculate the Grüneisen parameter of the target tissue based on the backscattered response signal.

12 Claims, 5 Drawing Sheets

(56) References Cited

U.S. PATENT DOCUMENTS

| | | | |
|---|---|---|---|
| 10,352,945 | B2 | 7/2019 | Cohen |
| 10,405,750 | B2 | 9/2019 | Wang |
| 11,045,169 | B2 | 6/2021 | Smith |
| 2007/0132846 | A1 | 6/2007 | Broad |
| 2008/0064921 | A1 | 3/2008 | Larkin |
| 2008/0091104 | A1 | 4/2008 | Abraham |
| 2008/0312561 | A1 | 12/2008 | Chauhan |
| 2009/0021724 | A1* | 1/2009 | Mahadevan-Jansen .................. G01N 21/65 356/73 |
| 2009/0048515 | A1 | 2/2009 | Suri |
| 2010/0001171 | A1* | 1/2010 | Matsuo ................ G02B 21/245 250/201.3 |
| 2010/0245769 | A1 | 9/2010 | Zhang |
| 2010/0268042 | A1 | 10/2010 | Wang |
| 2011/0098572 | A1 | 4/2011 | Chen |
| 2011/0282192 | A1 | 11/2011 | Axelrod |
| 2013/0131487 | A1* | 5/2013 | Nagao ................. A61B 5/0095 600/407 |
| 2013/0190595 | A1* | 7/2013 | Oraevsky ............ A61B 5/0035 600/407 |
| 2015/0173618 | A1 | 6/2015 | Kusukame |
| 2015/0216420 | A1* | 8/2015 | Oraevsky ............. A61B 5/015 600/407 |
| 2016/0150968 | A1 | 6/2016 | Imai |
| 2016/0213258 | A1 | 7/2016 | Lashkari |
| 2017/0105617 | A1* | 4/2017 | Li .......................... A61B 3/103 |
| 2017/0138926 | A1 | 5/2017 | Chubykin |
| 2017/0327841 | A1 | 11/2017 | Deisseroth |
| 2017/0367682 | A1 | 12/2017 | Smith |
| 2018/0008243 | A1 | 1/2018 | Irisawa |
| 2018/0057396 | A1* | 3/2018 | Li ..................... C03B 37/02763 |
| 2018/0078235 | A1 | 3/2018 | Irisawa |
| 2018/0177408 | A1 | 6/2018 | Irisawa |
| 2018/0177409 | A1 | 6/2018 | Irisawa |
| 2018/0220895 | A1* | 8/2018 | Masaki ................ A61B 5/0095 |
| 2018/0259370 | A1* | 9/2018 | Fontaine ............ G01D 5/35354 |
| 2019/0000377 | A1 | 1/2019 | Lei |
| 2019/0046159 | A1 | 2/2019 | Smith |
| 2019/0110691 | A1 | 4/2019 | Smith |
| 2019/0282069 | A1 | 9/2019 | Smith |
| 2020/0163612 | A1 | 5/2020 | Ntziachristos |
| 2021/0022680 | A1 | 1/2021 | Harris |
| 2021/0181019 | A1* | 6/2021 | Chang .................... A61B 5/681 |
| 2021/0275140 | A1 | 9/2021 | Smith |
| 2021/0402040 | A1* | 12/2021 | Botts ...................... A61B 90/35 |
| 2022/0202293 | A1 | 6/2022 | Kim |
| 2023/0172443 | A1* | 6/2023 | Bec ..................... A61B 5/0035 356/479 |

OTHER PUBLICATIONS

Rousseau G, Gauthier B, Blouin A, Monchalin JP. (Non-contact biomedical photoacoustic and ultrasound imaging. J Biomed Opt. Jun. 2012;17(6):061217 hereinafter "Rousseau"). (Year: 2012).*

Guangyao Li, Zhendong Guo, and Sung-Liang Chen, "Miniature all-optical probe for large synthetic aperture photoacoustic-ultrasound imaging," Opt. Express 25, 25023-25035 (2017) (Year: 2017).*

Aguirre, A. et al., "Potential Role of Coregistered Photoacoustic and Ultrasound Imaging in Ovarian Cancer Detection and Characterization", Translational Oncology, Feb. 2011, vol. 4, No. 1, pp. 29-37 <DOI:10.1593/tlo.10187>.

Alcázar, J. et al., "Endometrial blood flow mapping using transvaginal power Doppler sonography in women with postmenopausal bleeding and thickened endometrium", Ultrasound in Obstetrics & Gynecology, Jun. 2003, vol. 21, No. 6, pp. 583-588 <DOI:10.1002/uog.143>.

Alcázar, J. et al., "Intratumoral blood flow analysis in endometrial carcinoma: correlation with tumor characteristics and risk for recurrence", Gynecological Oncology, Feb. 2002, vol. 84, No. 2, pp. 258-262 <DOI:10.1006/gyno.2001.6496>.

Alcázar, J. et al., "Three-dimensional power Doppler ultrasound scanning for the prediction of endometrial cancer in women with postmenopausal bleeding and thickened endometrium", American Journal of Obstetrics and Gynecology, Jan. 2009, vol. 200, No. 1, article 44.e (6 pages) <DOI:10.1016/j.ajog.2008.08.027>.

Alcázar, J. et al., "Three-dimensional ultrasound for assessing women with gynecological cancer: a systematic review", Gynecologic Oncology, Mar. 2011, vol. 120, No. 3, pp. 340-346 <DOI:10.1016/j.ygyno.2010.10.023>.

Amant, F. et al., "Endometrial Cancer", Lancet, Aug. 2005, vol. 366, No. 9484, pp. 491-505 <DOI:10.1016/S0140-6736 (05)67063-8>.

Annecchino et al., "Robotic Automation of In Vivo Two-Photon Targeted Whole-Cell Patch-Clamp Electrophysiology," Neuron 95, 1048-1055, Aug. 30, 2017.

Antonsen, S. et al., "Mri, Pet/Ct and ultrasound in the preoperative staging of endometrial cancer-a multicenter prospective comparative study", Gynecologic Oncology, Feb. 2013, vol. 128, No. 2, pp. 300-308 <DOI:10.1016/j.ygyno.2012.11.025>.

Aytac-Kipergil, E., Demirkiran, A., Uluc, N. et al. Development of a Fiber Laser with Independently Adjustable Properties for Optical Resolution Photoacoustic Microscopy. Sci Rep 6, 38674 (2016). https://doi.org/10.1038/srep38674, Published Dec. 8, 2016 (Year: 2016).

Bai, X et al., "Intravascular optical-resolution photoacoustic tomography with a 1.1 mm diameter catheter", PLoS One, Mar. 2014, vol. 9, No. 3, article e92463 (6 pages) <DOI:10.1371/journal.pone.0092463>.

Bando et al., Genetic voltage indicators. BMC biology, 17(1):71, 2019.

Bedner, R. et al., "Hysteroscopy with directed biopsy versus dilatation and curettage for the diagnosis of endometrial hyperplasia and cancer in perimenopausal women", European Journal of Gnyaecological Oncology, 2007, vol. 28, No. 5, pp. 400-402.

Bohndiek, S. et al., "Development and application of stable phantoms for the evaluation of photoacoustic imaging instruments", PLoS One, Sep. 2013, vol. 8, No. 9, article e75533 (14 pages) <DOI:10.1371/journal.pone.0075533>.

Burke, W. et al., "Endometrial cancer: a review and current management strategies: part II", Gynecologic Oncology, Aug. 2014, vol. 134, No. 2, pp. 393-402 <DOI: 10.1016/j.ygyno.2014.06.003>.

Cheng, W. et al., "Clinical application of intratumoral blood flow study in patients with endometrial carcinoma", Cancer, May 1998, vol. 82, No. 10, pp. 1881-1886 <DOI:10.1002/(SICI)1097-0142(May 15, 1998)82:10%3C1881::AID-CNCR10%3E3.0.CO;2-P>.

Clement, P., "The pathology of uterine smooth muscle tumors and mixed endometrial stromal-smooth muscle tumors: a selective review with emphasis on recent advances", International Journal of Gynecological Pathology, Jan. 2000, vol. 19, No. 1, pp. 39-55.

Davis et al., Viral mutagenesis as a means for generating novel proteins. Journal of virology, 84(3):1625-1630, 2010.

Emoto, M. et al., "Clinical usefulness of color Doppler ultrasound in patients with endometrial hyperplasia and carcinoma", Cancer, Feb. 2002, vol. 94, No. 3, pp. 700-706 <DOI:10.1002/cncr.10208>.

Fyles et al., Photoionophores derived from crown ether polycarboxylic acids: synthesis, ion binding, and spectroscopic characterization. Canadian journal of chemistry, 72(5):1246-1253, 1994.

Goldstein, S., "The role of transvaginal ultrasound or endometrial biopsy in the evaluation of the menopausal endometrium", American Journal of Obstetrics and Gynecology, Jul. 2009, vol. 201, No. 1, pp. 5-11 <DOI:10.1016/j.ajog.2009.02.006>.

Hochbaum et al., All-optical electrophysiology in mammalian neurons using engineered microbial rhodopsins. Nature methods, 11(8):825, 2014.

Jansen, K. et al., "Lipid detection in atherosclerotic human coronaries by spectroscopic intravascular photoacoustic imaging", Optics Express, Sep. 2013, vol. 21, No. 18, pp. 21472-21484 <DOI:10.1364/OE.21.021472>.

Jathoul, A. et al., "Deep in vivo photoacoustic imaging of mammalian tissues using a tyrosinase-based genetic reporter", Nature Photonics, Mar. 2015, vol. 9, No. 4, pp. 239-246 <DOI:10.1038/nphoton.2015.22>.

(56) References Cited

OTHER PUBLICATIONS

Karpiouk, A. et al., "Feasibility of in vivo intravascular photoacoustic imaging using integrated ultrasound and photoacoustic imaging catheter", Journal of Biomedical Optics, Sep. 2012, vol. 17, No. 9, article 096008 (7 pages) <DOI:10.1117/1.JBO.17.9.096008>.
Keshavarzi, A. et al., "Attenuation coefficient and sound speed in human myometrium and uterine fibroid tumors", Journal of Ultrasound in Medicine, May 2001, vol. 20, No. 5, pp. 473-480 <DOI:10.7863/jum.2001.20.5.473>.
Kim, C. et al., "In Vivo Molecular Photoacoustic Tomography of Melanomas Targeted by Bioconjugated Gold Nanocages", ACS Nano, Jul. 2010, vol. 4, No. 8, pp. 4559-4564 <DOI: 10.1021/nn100736c>.
Kodama, J. et al., "Correlation of presenting symptoms and patient characteristics with endometrial cancer prognosis in Japanese women", International Jounral of Gynecology & Obstetrics, Sep. 2005, vol. 91, No. 2, pp. 151-156 <DOI:10.1016/j.ijgo.2005.08.002>.
Kodandaramaiah et al., "Automated Whole-Cell Patch-Clamp Electrophysiology of Neurons In Vivo," Nature Methods vol. 9, No. 6, Jun. 2012, pp. 585-590.
Kodandaramaiah et al., "Multi-Neuron Intracellular Recording in Vivo Via Interacting Autopatching Robots," Elife 7 (2018): e24656.
Kruger, R et al., "Dedicated 3D photoacoustic breast imaging", Medical Physics, Nov. 2013, vol. 40, No. 11, article 113301 (8 pages) <DOI:10.1118/1.4824317>.
Kumar et al. Dual-view plane illumination microscopy for rapid and spatially isotropic imaging. Nature protocols, 9 (11):2555-2573, 2014.
Lao, Y. et al., "Noninvasive photoacoustic imaging of the developing vasculature during early tumor growth", Physics in Medicine and Biology, Aug. 2008, vol. 53, No. 15, pp. 4203-4212 <DOI: 10.1088/0031-9155/53/15/013>.
Lee, C. et al., "Angiogenesis of endometrial carcinomas assessed by measurement of intratumoral blood flow, microvessel density, and vascular endothelial growth factor levels", Obstetrics and Gynecology, Oct. 2000, vol. 96, No. 4, pp. 615-621.
Li, M. et al., "Simultaneous Molecular and Hypoxia Imaging of Brain Tumors in Vivo Using Spectroscopic Photoacoustic Tomography", Proceedings of the IEEE, Mar. 2008, vol. 96, No. 3, pp. 481-489 <DOI:10.1109/JPROC.2007.913515>.
Mallidi, S. et al., "Photoacoustic imaging in cancer detection, diagnosis, and treatment guidance", Trends in Biotechnology, May 2011, vol. 29, No. 5, pp. 213-221 <DOI:10.1016/j.tibtech.2011.01.006>.
Merz, E. et al., "Sonographic size of uterus and ovaries in pre- and postmenopausal women", Ultrasound in Obstetrics & Gynecology, Jan. 1996, vol. 7, No. 1, pp. 38-42 <DOI:10.1046/j.1469-0705.1996.07010038.x>.
Minta et al., Fluorescent indicators for cytosolic sodium. Journal of Biological Chemistry, 264(32):19449-19457, 1989.
Miranda et al. "Photoacoustic micropipette," Applied Phsyics Letters 113(26): 264103 (2018).
Miranda, C. et al., "Intrauterine photoacoustic and ultrasound imaging probe", Journal of Biomedical Optics, Apr. 2018, vol. 23, No. 4, article 046008 (9 pages) <DOI:10.1117/1.JBO.23.4.046008>.
Mishra et al., Near-infrared photoacoustic imaging probe responsive to calcium. Analytical chemistry, 88(22):10785-10789, 2016.
Morice, P. et al., "Endometrial Cancer", Lancet, Mar. 2016, vol. 387, No. 10023, pp. 1094-1108 <DOI:10.1016/S0140-6736(15)00130-0>.
Nakahara et al., "Fluorometric sensing of alkali metal and alkaline earth metal cations by novel photosensitive monoazacryptand derivatives in aqueous micellar solutions," Organic & biomolecular chemistry, 3(9):1787-1794, 2005.
Nicholson, W. et al., "Patterns of ambulatory care use for gynecologic conditions: a national study", American Journal of Obstetrics and Gynecology, Mar. 2001, vol. 184, No. 4, pp. 523-530 <DOI:10.1067/mob.2001.111795>.

Ning, B. et al., "Simultaneous photoacoustic microscopy of microvascular anatomy, oxygen saturation, and blood flow", Optics Letters, Mar. 2015, vol. 40, No. 6, pp. 910-913 <DOI:10.1364/OL.40.000910>.
Office Action (Final Rejection) dated Feb. 7, 2023 for U.S. Appl. No. 17/401,640 (pp. 1-49).
Office Action (Non-Final Rejection) dated Dec. 15, 2022 for U.S. Appl. No. 17/329,649 (pp. 1-18).
Office Action dated Jun. 2, 2023 for U.S. Appl. No. 17/329,649 (pp. 1-22).
Piatkevich et al. A robotic multidimensional directed evolution approach applied to fluorescent voltage reporters. Nature chemical biology, 14(4):352-360, 2018.
Pitrone et al., Openspim: an open-access light-sheet microscopy platform. Nature methods, 10(7):598-599, 2013.
Ribatti, D. et al., "Neovascularization and mast cells with tryptase activity increase simultaneously with pathologic progression in human endometrial cancer", American Journal of Obstetrics & Gynecology, Dec. 2005, vol. 193, No. 6, pp. 1961-1965 <DOI:10.1016/j.ajog.2005.04.055>.
Salvesen, H. et al., "Independent prognostic importance of microvessel density in endometrial carcinoma", British Journal of Cancer, Apr. 1998, vol. 77, No. 7, pp. 1140-1144 <DOI:10.1038/bjc.1998.189>.
Scarcelli et al., Conformal Brillouin Microscopy for Three-Dimensional Mechanical Imaging, 12 pages.
Schwarz, M. et al., "Three-dimensional multispectral optoacoustic mesoscopy reveals melanin and blood oxygenation in human skin in vivo", Journal of Biophotonics, Jan. 2016, vol. 9, No. 1-2, pp. 55-60 <DOI:10.1002/jbio.201500247>.
Sethuraman, S. et al., "Intravascular Photoacoustic Imaging Using an IVUS Imaging Catheter", IEEE Transactions on Ultrasonics, Ferroelectrics, and Frequency Control, May 2007, vol. 54, No. 5, pp. 978-986 <DOI:10.1109/TUFFC.2007.343>.
Shao et al., "Spatially-Resolved Brillouin Spectroscopy Reveals Biomechanical Abnormalities in Mild to Advanced Keratoconus in Vivo," Sci Rep 9, 7467 (2019).
Shelton et al., Picosecond Ultrasonic Measurement of the Velocity of Phonons in Water, Physica Status Solidi (b), 242(7):1379-1382, 2005.
Siegal, R. et al., "Cancer statistics, 2016", CA—Cancer Journal, Jan./Feb. 2016, vol. 66, No. 1, pp. 7-30 <DOI:10.3322/caac.21332>.
Siphanto, R. et al., "Serial noninvasive photoacoustic imaging of neovascularization in tumor angiogenesis", Optics Express, Jan. 2005, vol. 13, No. 1, pp. 89-95 <DOI:10.1364/OPEX.13.000089>.
Smith-Bindman, R. et al., "Endovaginal ultrasound to exclude endometrial cancer and other endometrial abnormalities", JAMA, Nov. 1998, vol. 280, No. 17, pp. 1510-1517.
Stewart, E. et al., "Uterine Fibroids", Lancet, Jan. 2001, vol. 357, No. 9252, pp. 293-298 <DOI:10.1016/S0140-6736(00)03622-9>.
Subach et al., Directed molecular evolution to design advanced red fluorescent proteins. Nature methods, 8 (12):1019, 2011.
Suk et al., "Closed-Loop Real-Time Imaging Enables Fully Automated Cell-Targeted Patch-Clamp Neural Recoding In Vivo," Neuron 95, 1037-1047, Aug. 30, 2017.
Symonds, I., "Ultrasound, hysteroscopy and endometrial biopsy in the investigation of endometrial cancer", Best Practice & Research. Clinical Obstetrics & Gynecology, Jun. 2001, vol. 15, No. 3, pp. 381-391 <DOI:10.1053/beog.2000.0183>.
Tamai, K. et al., "Diffusion-weighted MR imaging of uterine endometrial cancer", Journal of Magnetic Resonance Imaging: JMRI, Sep. 2007, vol. 26, No. 3, pp. 682-687 <DOI:10.1002/jmri.20997>.
Timmermans, A. et al., "Endometrial thickness measurement for detecting endometrial cancer in women with postmenopausal bleeding: a systematic review and meta-analysis", Obstetrics and Gynecology, Jul. 2010, vol. 116, No. 1, pp. 160-167 <DOI: 10.1097/AOG.0b013e3181e3e7e8>.
Treeby et al., Photoacoustic tomography in absorbing acoustic media using time reversal. Inverse Problems, 26 (11):115003, 2010.

(56) References Cited

OTHER PUBLICATIONS

Tsien, New calcium indicators and buffers with high selectivity against magnesium and protons: design, synthesis, and properties of prototype structures. Biochemistry, 19(11):2396-2404, 1980.

Wang, B. et al., "Intravascular photoacoustic imaging of lipid in atherosclerotic plaques in the presence of luminal blood", Optics Letters, Apr. 2012, vol. 37, No. 7, pp. 1244-1246 <DOI:10.1364/OL.37.001244>.

Wang, B. et al., "Intravascular Photoacoustic Imaging", IEEE Journal of Selected Topics in Quantum Electronics, May/Jun. 2010, vol. 16, No. 3, pp. 588-599 <DOI:10.1109/JSTQE.2009.2037023>.

Wang, L. et al., "Photoacoustic Tomography: In Vivo Imaging from Organelles to Organs", Science, Mar. 2012, vol. 335, No. 6075, pp. 1458-1462 <DOI:10.1126/science.1216210>.

Wang, P. et al., "High-speed intravascular photoacoustic imaging of lipid-laden atherosclerotic plaque enabled by a 2-kHz barium nitrite raman laser", Scientific Reports, Nov. 2014, vol. 4, No. 6889, 7 pages <DOI:10.1038/srep06889>.

Wang, X. et al., "Noninvasive imaging of hemoglobin concentration and oxygenation in the rat brain using high-resolution photoacoustic tomography", Journal of Biomedical Optics, Mar./Apr. 2006, vol. 11, No. 2, article 024015 (9 pages) <DOI:10.1117/1.2192804>.

Wissmeyer et al., Looking at sound: optoacoustics with all-optical ultrasound detection. Light: Science & Applications, 7(1):1-16, 2018.

Wright, D. et al., "Contemporary management of endometrial cancer", Lancet, Apr. 2012, vol. 379, No. 9823, pp. 1352-1360 <DOI:10.1016/S0140>.

Wu et al., Dynamic dimensional synthesis of a precision 6-DOF parallel manipulator, 2012 IEEE International Conference on Mechatronics and Automation, DOI: 10.1109/ICMA.2012.6283250, Date of Conference: Aug. 5-8, 2012, Date Added to IEEE Xplore: Aug. 27, 2012 (Year: 2012).

Xu, M. et al., "Photoacoustic imaging in biomedicine", Review of Scientific Instruments, Feb. 2006, vol. 77, No. 4, article 041101 (23 pages) <DOI:10.1063/1.2195024>.

Yang, J. et al., "Photoacoustic Endoscopy", Optics Letters, May 2009, vol. 34, No. 10, pp. 1591-1593.

Yang, J. et al., "Simultaneous functional photoacoustic and ultrasonic endoscopy of internal organs in vivo", Nature Medicine, Aug. 2012, vol. 18, No. 8, pp. 1297-1302 <DOI: 10.1038/nm.2823>.

Yang, J. et al., "Three-dimensional photoacoustic endoscopic imaging of the rabbit esophagus", PLoS One, Apr. 2015, vol. 10, No. 4, article e0120269 (15 pages) <DOI:10.1371/journal.pone.0120269>.

Yang, J. et al., "Volumetric photoacoustic endoscopy of upper gastrointestinal tract: ultrasonic transducer technology development", Proceedings of SPIE, Feb. 2011, vol. 7899, article 78990D (6 pages) <DOI:10.1117/12.875377>.

Yao, J. et al., "Label-free oxygen-metabolic photoacoustic microscopy in vivo", Journal of Biomedical Optics, Jul. 2011, vol. 16, No. 7, article 076003 (12 pages) <DOI:10.1117/1.3594786>.

Yeh, C. et al., "Microvascular quantification based on contour-scanning photoacoustic microscopy", Journal of Biomedical Optics, Sep. 2014, vol. 19, No. 9, article 096011 (7 pages) <DOI:10.1117/1.JBO.19.9.096011>.

Zhang, E. et al., "A miniature all-optical photoacoustic imaging probe", Proceedings of SPIE, Feb. 2011, vol. 1899, article 78991F (7 pages) <DOI:10.1117/12.874883>.

Zhang, E. et al., "In vivo high-resolution 3D photoacoustic imaging of superficial vascular anatomy", Physics in Medicine and Biology, Feb. 2009, vol. 54, No. 4, pp. 1035-1046 <DOI:10.1088/0031-9155/54/4/014>.

* cited by examiner

DUAL BRILLOUIN-PHOTOACOUSTIC MICROSCOPY

CROSS-REFERENCE TO RELATED APPLICATIONS

This application claims the benefit of priority to U.S. Provisional Application No. 63/117,002 entitled "Dual Brillouin-Photoacoustic Microscopy," filed Nov. 23, 2020, which is incorporated herein by reference in its entirety.

TECHNICAL FIELD

The present disclosure relates generally to methods, systems, and apparatuses related to detecting and measuring biomechanical properties of cells and tissues. The disclosed techniques may be applied to various tissues as a clinical tool, for example, to investigate ocular tissue in a patient.

BACKGROUND

The ability to measure biomechanical properties of selected cells and tissues is essential in order to gain immediate insight into cellular function, development, and disease progression. In particular, tools for biomechanical measurement may be useful for assessing ocular tissue because biomechanics may provide insight into the development and progression of various eye diseases and refractive errors. For example, Keratoconus is a common disease that distorts vision due to local thinning of the cornea that causes the cornea to bulge into a conical shape. In another example, Myopia, i.e., near-sightedness, may be monitored and detected through investigation of the weakening of the sclera. While various tools have been developed for the purpose of assessing tissue properties, adoption of such tools for measuring biomechanical properties in a clinical setting has proven difficult.

Photoacoustic microscopy (PAM) is based on the principle of the photoacoustic effect, which is defined as the generation of acoustic waves caused by thermal expansion due to optical absorption. In photoacoustic microscopy, the generated acoustic waves are minimally affected by scattering and/or attenuation, thereby allowing for absorption-based contrast at great depths beyond the capability of conventional imaging modalities. Further, recent advancements in PAM enable contrast-free image reconstructions of subcellular biological structures. However, currently available PAM techniques nonetheless require a transducer to make contact with a sample either directly or through a coupling medium to allow for signal acquisition. As such, while currently available PAM techniques may be useful in research applications, they may not translate successfully to some clinical applications.

Another investigative tool, Brillouin microscopy, operates based on the principle of Brillouin scattering, which occurs when light interacts with acoustic waves. Advances in Brillouin microscopy have led to improved clinical information about the biomechanical state of biological tissue, e.g., human tissue. The acoustic waves may modulate the refractive index periodically such that a Doppler frequency shift after light reflection may be measured. Advantageously, Brillouin scattering is remarkably sensitive to small spontaneous pressure waves. Despite advances, however, Brillouin microscopy may be critically limited by signal intensity and depth, thus limiting the utility of Brillouin microscopy for analyzing biomechanical properties in clinical settings. Further, measurement times in conventional Brillouin microscopy techniques may be relatively long, making such techniques less than ideal for clinical applications that typically rely on spontaneous acoustic waves that form in biological tissue.

Additional conventional methods exist for determining the mechanobiology of cells and living tissues, including atomic force microscopy, optical trapping, magnetic probing, focal adhesion, strain arrays, microfluidic chambers, and/or magnetic resonance elastography. However, these methods are often impractical for in vivo applications because they require physical contact with the sample and/or manipulation of exogenous probes for proper measurements.

As such, it would be advantageous to have a non-contact method and/or system for measuring biomechanical properties of cells and tissues that is capable of measuring at greater tissue depth and without reliance on a transducer or coupling medium.

SUMMARY

A system for calculating a Grüneisen parameter of a target tissue is provided. The system comprises a first light source configured to emit a first light signal to the target tissue, wherein the first light signal is configured to generate an acoustic signal in the target tissue; a second light source configured to emit a second light signal to the target tissue, wherein interaction of the second light signal with the acoustic signal causes backscattering of the second light signal to generate a backscattered light signal; a light sensor configured to detect the backscattered light signal; a processor; and a non-transitory, computer-readable medium storing instructions that, when executed, cause the processor to: receive one or more electrical signals indicative of the backscattered light signal from the light sensor; and calculate, based on the backscattered light signal, the Grüneisen parameter of the target tissue.

According to some embodiments, the first light source comprises a pulsed laser. According to additional embodiments, the first light signal has a frequency of about 1 kHz or greater.

According to some embodiments, the first light signal comprises one of an ultraviolet light signal, a visible light signal, and a near infrared light signal.

According to some embodiments, the second light source comprises a continuous wave laser. According to some embodiments, the second light signal comprises a near infrared light signal.

According to some embodiments, the system further comprises a Brillouin spectrometer including the second light source and the light sensor.

According to some embodiments, the first light signal is configured to induce photoacoustic effects in the target tissue, thereby causing generation of the acoustic signal. According to additional embodiments, the first light signal is configured to be absorbed by one or more subcellular components of the target tissue, thereby resulting in the photoacoustic effects. According to further embodiments, the one or more subcellular components comprise one or more of DNA, RNA, cytoplasm, and a myelin sheath.

According to some embodiments, a frequency of the backscattered light signal is different from a known frequency of the second light signal. According to additional embodiments, the instructions that cause the processor to calculate the Grüneisen parameter comprise instructions that, when executed, cause the processor to: determine a frequency shift of the backscattered light signal with respect to the second light signal; calculate a magnitude of the acoustic signal based on the frequency shift; and calculate the Grüneisen parameter based on the magnitude of the acoustic signal. According to further embodiments, the instructions that cause the processor to determine a frequency shift of the backscattered light signal comprise instructions that, when executed, cause the processor to: determine the frequency of the backscattered light signal; and calculate the frequency shift based on the frequency of the backscattered light signal and the known frequency of the second light signal. According to further embodiments, the instructions that cause the processor to calculate the Grüneisen parameter comprise instructions that, when executed, cause the processor to calculate the Grüneisen parameter based on the magnitude of the acoustic signal, a fluence of the first light signal, and an absorption coefficient of the target tissue.

According to some embodiments, the instructions, when executed, further cause the processor to: receive, for each of a plurality of locations of the target tissue, one or more electrical signals indicative of the backscattered light signal associated with the location; and calculate, based on the backscattered light signal, the Grüneisen parameter of the target tissue for each location. According to additional embodiments, the instructions, when executed, further cause the processor to construct a spatial map of the Grüneisen parameter across the plurality of locations of the target tissue.

According to some embodiments, the system further comprises a display, wherein the instructions, when executed, further cause the processor to display the calculated Grüneisen parameter on the display.

According to some embodiments, the first light source and the second light source are configured to concentrically emit the first light signal and the second light signal to the target tissue.

A method of calculating a Grüneisen parameter at one or more locations of a target tissue is provided. The method comprises emitting a first light signal to each location of the target tissue, wherein the first light signal is absorbed by the target tissue, thereby generating an acoustic signal at the location; emitting a second light signal to each location of the target tissue, wherein the second light signal interacts with the acoustic signal, thereby generating a backscattered light signal; detecting, by a light sensor, the backscattered response signal at each location; and calculating, based on the backscattered response signal, the Grüneisen parameter for each location of the target tissue.

According to some embodiments, the first light signal is emitted by a pulsed laser.

According to some embodiments, the first light signal comprises one of an ultraviolet light signal, a visible light signal, and a near infrared light signal.

According to some embodiments, the second light signal is emitted by a continuous wave laser.

According to some embodiments, the second light signal comprises a near infrared light signal.

According to some embodiments, the first light signal induces photoacoustic effects in the target tissue, thereby causing generation of the acoustic signal. According to additional embodiments, the first light signal is absorbed by one or more subcellular components of the target tissue to induce the photoacoustic effects. According to further embodiments, the one or more subcellular components comprise one or more of DNA, RNA, cytoplasm, and a myelin sheath.

According to some embodiments, a frequency of the backscattered light signal is different from a known frequency of the second light signal. According to additional embodiments, calculating the Grüneisen parameter for each location of the target tissue comprises: determining a frequency shift of the backscattered light signal with respect to the second light signal; calculating a magnitude of the acoustic signal based on the frequency shift; and calculating the Grüneisen parameter based on the magnitude of the acoustic signal. According to further embodiments, determining a frequency shift of the backscattered light signal comprises determining the frequency of the backscattered light signal; and calculating the frequency shift based on the frequency of the backscattered light signal and the known frequency of the second light signal. According to further embodiments, calculating the Grüneisen parameter is further based on a fluence of the first light signal and an absorption coefficient of the target tissue.

According to some embodiments, the method further comprises displaying the calculated Grüneisen parameter on a display.

According to some embodiments, the first light signal and the second light signal are concentrically emitted to the location of target tissue.

According to some embodiments, the one or more locations comprise a plurality of locations of the target tissue. According to additional embodiments, the method further comprises constructing a spatial map of the Grüneisen parameter across the plurality of locations of the target tissue. According to further embodiments, the method further comprises displaying the constructed spatial map on a display.

BRIEF DESCRIPTION OF THE DRAWINGS

The accompanying drawings, which are incorporated in and form a part of the specification, illustrate the embodiments of the technology and together with the written description serve to explain the principles, characteristics, and features of the technology.

DETAILED DESCRIPTION

Figure 1:
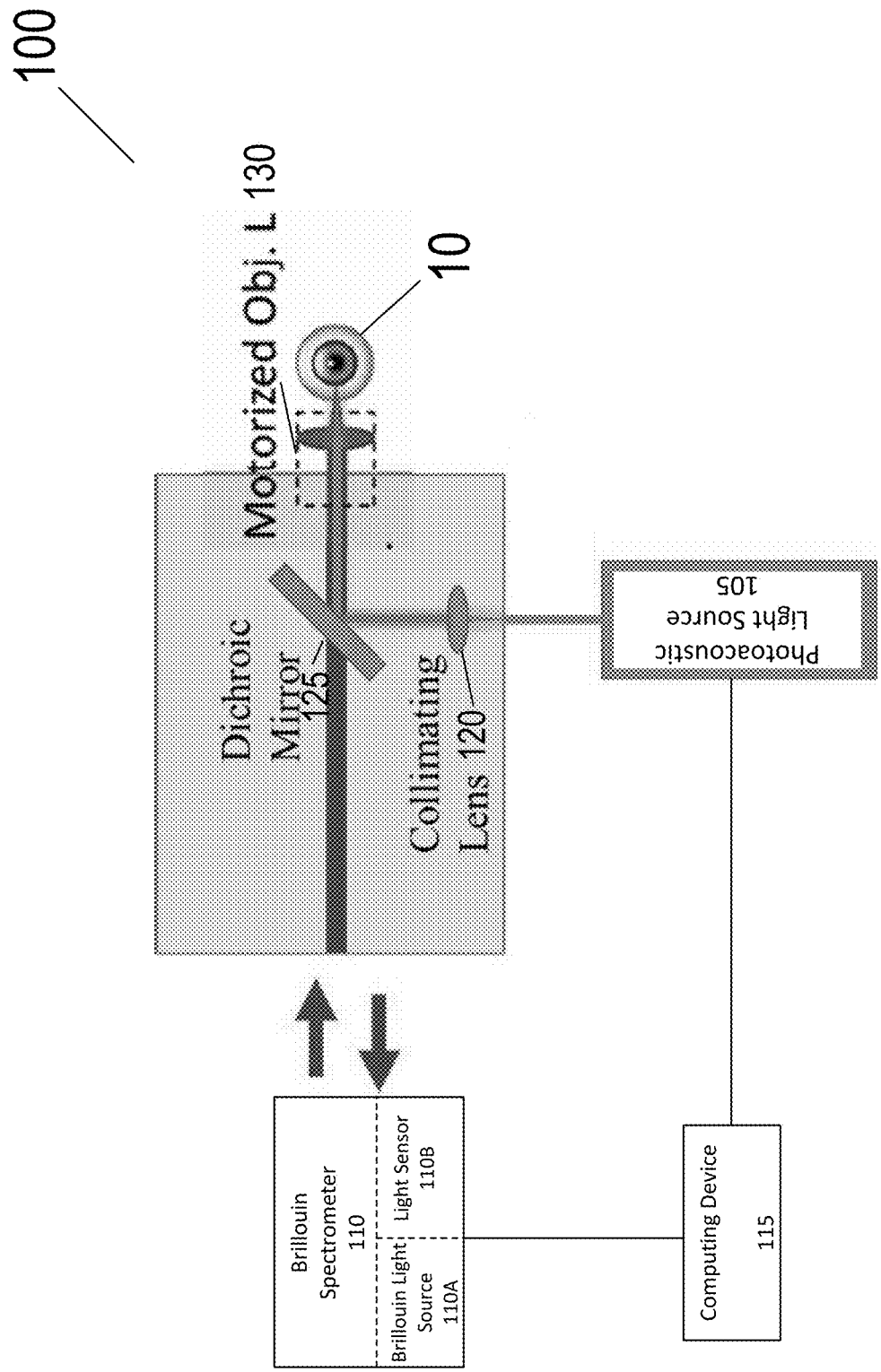
FIG. 1 depicts an illustrative system for measuring biomechanical properties of a tissue in accordance with an embodiment.

This disclosure is not limited to the particular systems, devices and methods described, as these may vary. The terminology used in the description is for the purpose of describing the particular versions or embodiments only, and is not intended to limit the scope. Such aspects of the disclosure be embodied in many different forms; rather, these embodiments are provided so that this disclosure will be thorough and complete, and will fully convey its scope to those skilled in the art.

As used in this document, the singular forms "a," "an," and "the" include plural references unless the context clearly dictates otherwise. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

As will be understood by one skilled in the art, for any and all purposes, such as in terms of providing a written description, all ranges disclosed herein are intended as encompassing each intervening value between the upper and lower limit of that range and any other stated or intervening value in that stated range. All ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells as well as the range of values greater than or equal to 1 cell and less than or equal to 3 cells. Similarly, a group having 1-5 cells refers to groups having 1, 2, 3, 4, or 5 cells, as well as the range of values greater than or equal to 1 cell and less than or equal to 5 cells, and so forth.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

By hereby reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by hereby reserving the right to proviso out or exclude any individual substituents, structures, or groups thereof, or any members of a claimed group, less than the full measure of this disclosure can be claimed for any reason.

All percentages, parts and ratios of a composition are based upon the total weight of the composition and all measurements made are at about 25° C., unless otherwise specified.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by $\frac{1}{10}$ of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the present disclosure include equivalents to the recited values, e.g., variations in the numerical quantity of such values that can occur, but would be recognized to be equivalents by a person skilled in the art. Where the context of the disclosure indicates otherwise, or is inconsistent with such an interpretation, the above-stated interpretation may be modified as would be readily apparent to a person skilled in the art. For example, in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," et cetera). Further, the transitional term "comprising," which is synonymous with "including," "containing," or "characterized by," is inclusive or open-ended and does not exclude additional, unrecited elements or method steps. While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The term "patient" and "subject" are interchangeable and may be taken to mean any living organism which contains neural tissue. As such, the terms "patient" and "subject" may include, but is not limited to, any non-human mammal, primate or human. A subject can be a mammal such as a primate, for example, a human. The term "subject" includes domesticated animals (e.g., cats, dogs, etc.), livestock (e.g., cattle, horses, swine, sheep, goats, etc.), and laboratory animals (e.g., mice, rabbits, rats, gerbils, guinea pigs, possums, etc.). In some embodiments, the patient or subject is an adult, child or infant. In some embodiments, the patient or subject is a human.

The term "tissue" refers to any aggregation of similarly specialized cells which are united in the performance of a particular function.

The term "disorder" is used in this disclosure to mean, and is used interchangeably with, the terms disease, condition, or illness, unless otherwise indicated.

The term "real-time" is used to refer to calculations or operations performed on-the-fly as events occur or input is received by the operable system. However, the use of the term "real-time" is not intended to preclude operations that cause some latency between input and response, so long as the latency is an unintended consequence induced by the performance characteristics of the machine.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

Throughout this disclosure, various patents, patent applications and publications are referenced. The disclosures of these patents, patent applications and publications are incorporated into this disclosure by reference in their entireties in order to more fully describe the state of the art as known to those skilled therein as of the date of this disclosure. This disclosure will govern in the instance that there is any inconsistency between the patents, patent applications and publications cited and this disclosure.

As discussed herein, it may be desirable to perform non-contact biomechanical measurements for living cells and/or tissue in a clinical setting at sufficient depths for evaluation and/or diagnosis of tissue. Preferably, a non-contact system for collecting biomechanical measurements will allow for greater depth of imaging and sub-micron diffraction-limited resolution. Moreover, contrast-free imaging techniques that may be performed in the same or less time as conventional imaging techniques would be advantageous in a clinical setting.

Referring now to FIG. 1, an illustrative system for calculating biomechanical properties of a tissue is depicted in accordance with an embodiment. As shown in FIG. 1, the system 100 may comprise a photoacoustic light source 105, a Brillouin spectrometer 110 including a Brillouin light source 110A and a light sensor 110B, and a computing device 115. The system 100 may further comprise electrical circuitry and additional components for transmitting light, detecting light, and/or receiving and transmitting electrical signals between components of the system 100 as would be known to a person having an ordinary level of skill in the art.

In some embodiments, the photoacoustic light source 105 is a laser. In some embodiments, the photoacoustic light source 105 is a high-intensity laser. For example, the photoacoustic light source 105 may be a pulsed laser such as a nanosecond pulsed laser. In some embodiments, the laser is a neodymium-doped yttrium aluminum garnet (Nd:YAG) laser. In some embodiments, the laser is a titanium-sapphire (TiSa) laser. In some embodiments, the laser may be configured to provide fast excitation and a resultant photoacoustic signal. However, in some embodiments, the light source may be a continuous wave laser. In some embodiments, the continuous wave laser may be configured to emit light at a continuous power level to generate a resultant photoacoustic signal. In some embodiments, the continuous wave laser may be configured to emit light at a modulated level to generate a resultant photoacoustic signal.

Referring once again to FIG. 1, the Brillouin spectrometer 110 may comprise various components and features in order to emit a light signal to the target tissue 10 and detect backscattered light in response thereto. As shown in FIG. 1, the Brillouin spectrometer 110 comprises at least a Brillouin light source 110A and a light sensor 110B. However, the Brillouin spectrometer 110 may comprise various additional components as would be known to a person having an ordinary level of skill in the art. For example, the Brillouin spectrometer 110 may comprise a Brillouin spectrometer as described in the article entitled "Spatially-Resolved Brillouin Spectroscopy Reveals Biomechanical Abnormalities in Mild to Advanced Keratoconus In Vivo" by Shao, P., Eltony, A. M., Seiler, T. G. et al., Sci Rep 9, 7467 (2019), which is incorporated by reference herein in its entirety.

In some embodiments, the Brillouin light source 110A comprises a continuous wave laser configured to emit light at a predetermined wavelength and/or frequency. For example, the Brillouin light source 110A may be a single-frequency tunable laser with an output spectrum locked to a near-infrared wavelength of about 780 nm. In some embodiments, the light emitted by the light source 110A may be filtered by an etalon (i.e., a Fabry-Pérot interferometer).

The light sensor 110B may be configured to detect a response signal (i.e., backscattered light) in response to the light emitted by the Brillouin light source 110A. In some embodiments, the light sensor 110B comprises a high-resolution, two-stage VIPA spectrometer. However, the light sensor 110B may be any sensor capable of detecting a frequency of the backscattered light.

In some embodiments, the photoacoustic light source 105 and/or the Brillouin light source 110A may be configured to be directed towards a target tissue 10 through one or more additional components. Similarly, the light sensor 110B may be configured to receive the response signal through one or more additional components. For example, as shown in FIG. 1, the system 100 may further comprise a collimating lens 120, a dichroic mirror 125, and a motorized objective lens 130 for focusing and directing light emitted from the photoacoustic light source 105 and/or the Brillouin light source 110A towards the target tissue 10. Furthermore, the response signal may be received by the light sensor 110B through the dichroic mirror 125 and/or the motorized objective lens 130. While the system 100 is depicted as including one collimating lens 120, one dichroic mirror 125, and one motorized objective lens 130, it should be understood that a plurality of one or more of these components may be included in the system 100 to provide a desired effect on the emitted light and/or response signal as would be apparent to a person having an ordinary level of skill in the art. For example, the photoacoustic light source 105 and the Brillouin light source 110A may be configured to emit light through separate sets of components to reach the target tissue 10. In some embodiments, the system 100 further comprises one or more emission filters and/or excitation filters configured to adjust a wavelength and/or frequency of light from the photoacoustic light source 105 and/or the Brillouin light source 110A to deliver a desired wavelength and/or frequency of light to the target tissue 10.

As described, the photoacoustic light source 105 and the Brillouin light source 110A may be configured and oriented with respect to one another in a variety of manners. In embodiments where the photoacoustic light source 105 and the Brillouin light source 110A emit different wavelengths of light, the light sources 105/110A may be utilized in a configuration similar to that utilized in conventional fluorescent microscopes (e.g., as shown in FIG. 1). However, in some embodiments, the photoacoustic light source 105 and the Brillouin light source 110A are configured to emit the same wavelength of light. Accordingly, a series of waveplates and polarizing beam splitters may be implemented similar to conventional Brillouin microscopy setups.

In some embodiments, the photoacoustic light source 105 and the Brillouin light source 110A may be placed in a dual axis configuration where parallel beams are introduced into the same objective lens, resulting in a slight beam cross angle.

In some embodiments, the photoacoustic light source 105, the Brillouin light source 110A, and/or the light sensor 110B may be combined and/or consolidated as an optical unit comprising the collimating lens 120, the dichroic mirror 125, the motorized objective lens 130, and/or any number of additional components. In some embodiments, the components of the optical unit may be housed in an optical enclosure.

In some embodiments, the system 100 may further comprise one or more fibers (not shown) for transmitting light between components of the system 100. In some embodiments, the one or more fibers comprise optical fibers. In some embodiments, the one or more fibers comprise multi-mode optical fibers. In some embodiments, the one or more fibers comprise single mode optical fibers. For example, the photoacoustic light source 105 may be coupled to other components of the system 100 via a multi-mode optical fiber. In another example, the Brillouin light source 110A and/or the light sensor 110B may each be coupled to other components of the system via single mode optical fibers, e.g., polarization maintaining single-mode fibers. However, additional and alternative types and/or configurations of fibers and transmission conduits are contemplated herein as would be known to a person having an ordinary level of skill in the art.

In some embodiments, one or more characteristics of the light emitted by the photoacoustic light source 105 may be adjusted. In some embodiments, the intensity of light signal may be adjusted. In some embodiments, the frequency of the light signal may be adjusted. In some embodiments, the color or wavelength of the light signal may be adjusted. In some embodiments, the characteristics of the emitted light signal may be fixed. Some parameters of the emitted light signal (e.g., intensity) may affect the feedback range of the system 100, i.e., the distance at which resultant photoacoustic signals may be effective for inducing Brillouin scattering of the light emitted by the Brillouin light source 110A. It may be necessary to induce Brillouin scattering in the light emitted by the Brillouin light source 110A in order to assess biomechanical properties of the target tissue 10 as further described herein.

Figure 2A:
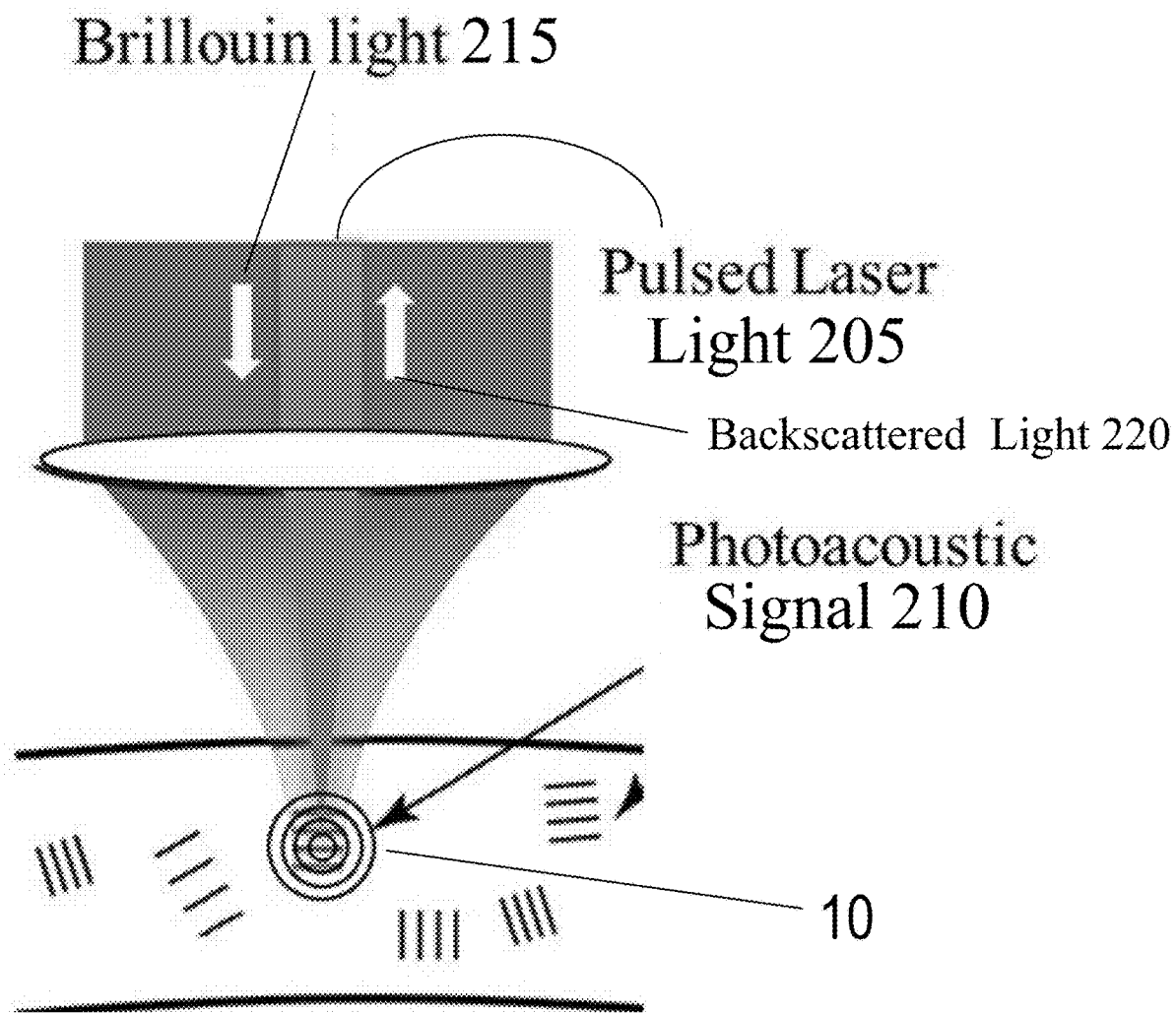
FIG. 2A depicts an exemplary setup for measuring Brillouin light scattering from a target tissue is depicted in accordance with an embodiment.
Figure 2B:
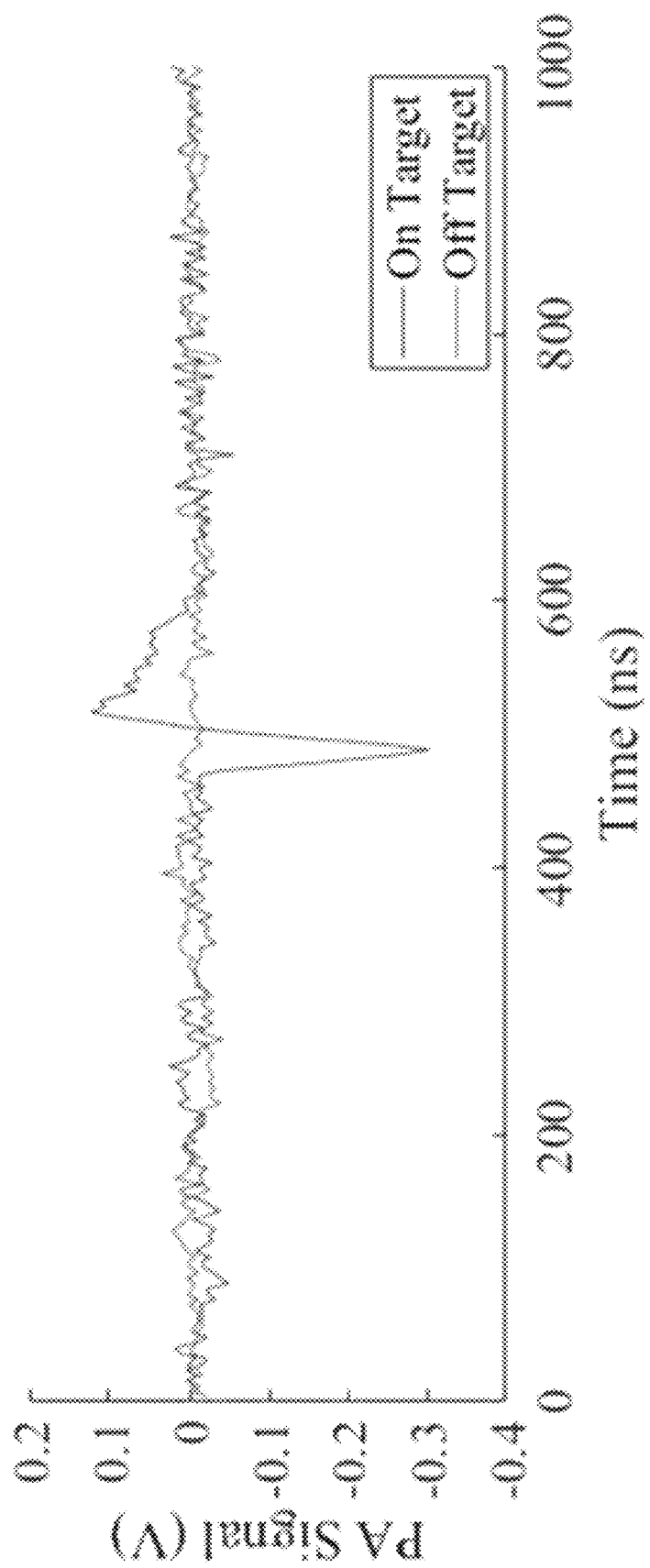
FIG. 2B depicts a typical photoacoustic signal detected at a target tissue in accordance with an embodiment.

Referring now to FIG. 2A, an exemplary setup for measuring Brillouin light scattering from a target tissue is depicted in accordance with an embodiment. As shown, pulsed laser light 205 from the photoacoustic light source 105 may be delivered to the target tissue 10 in order to induce a photoacoustic effect at the target issue 10, i.e., an emitted photoacoustic signal 210 in response to the pulsed laser light 205 absorbed by the target tissue 10. FIG. 2B depicts a typical photoacoustic signal detected at a target tissue 10 in accordance with an embodiment. The emitted light signal 205 creates a photoacoustic signal 210. When molecules (e.g., a chromophore or another light-absorbing component contained within biological cells or tissues) absorb light at specific wavelengths, the result is molecular excitation and thermal expansion of the tissue that generates an acoustic wave.

In some embodiments, the photoacoustic effect may advantageously be induced without the use of a contrast agent. Although a contrast agent is typically applied to a target tissue to induce the photoacoustic effect, several cellular components may have strong absorption peaks in the ultraviolet (UV), visible, and/or near infrared (NIR) range. For example, cellular components such as DNA, RNA, cytoplasm, and/or myelin sheath may have strong absorption peaks in these wavelength ranges. Accordingly, the cellular components may serve as endogenous chromophores (i.e., highly absorbent molecules) in order to induce the photoacoustic effect without the need for a contrast agent (i.e., contrast free pressure induction). In additional embodiments, a contrast agent comprising a chromophore may be applied to the target tissue, thereby causing increased absorption of light at the specific emitted wavelength and inducing the photoacoustic effect in the tissue.

Referring once again to FIG. 2A, a continuous wave light signal 215 from the Brillouin light source 110A may be delivered to the target tissue 10 to induce Brillouin backscattering. As shown, in some embodiments, the photoacoustic light source 105 and the Brillouin light source 110A may be configured to concentrically emit the respective light signals to the target tissue 10. The continuous wave light signal 215 may be backscattered as backscattered light signal 220 (i.e., the response signal). According to the principles of Brillouin backscattering, the continuous wave light signal 215 may undergo a frequency shift by its interaction with the photoacoustic signal 210 induced by the pulsed laser light 205. In essence, the acoustic waves may periodically modulate the refractive index of the target tissue, thereby causing a measurable Doppler frequency shift in the backscattered light signal 220. Therefore, the backscattered light signal 220 in FIG. 2A may detected as a response signal by the light sensor 110B and characterized, e.g., by determining a frequency thereof. The frequency shift of the backscattered light signal 220 with respect to the emitted continuous wave light signal 215 may be indicative of one or more properties of the target tissue 10, e.g., the Grüneisen parameter.

Advantageously, emitted light is remarkably sensitive to pressure waves such that Brillouin scattering occurs in response to even small, spontaneous pressure waves. In cases where the photoacoustic effect is induced as described herein, the resultant pressure waves may be greater than spontaneous pressure waves by several orders of magnitude. For example, spontaneous pressure waves may be up to about 100 Pa while photoacoustic waves may up to about 10 kPa. Accordingly, the technique as described may demonstrate very high sensitivity and result in greater shifts in frequency, thereby enabling calculation of the Grüneisen parameter with high accuracy and/or resolution. Furthermore, greater sensitivity may allow signal acquisition time to be reduced dramatically, thereby improving the feasibility of such techniques for clinical applications.

Returning to FIG. 1, the system 100 comprises a computing device 115 configured to communicate with one or more components of the system 100. For example, the computing device may comprise one or more processors and a non-transitory, computer-readable medium storing instructions that may be executed by the processor. The one or more processors may be configured to receive a detected response signal from the light sensor 110B. In some embodiments, the computing device 115 may further communicate with the photoacoustic light source 105 and/or the Brillouin light source 110A. For example, the computing device 115 may communicate with the light sources 105/110A by transmitting electrical signals thereto to activate the light sources 105/110A and cause light to be emitted therefrom in a controlled manner.

The computing device 115 may be configured to receive the detected response signal from the light sensor 110B and calculate, based on the response signal, a Grüneisen parameter of the target tissue 10. In some embodiments, calculating the Grüneisen parameter comprises determining a frequency shift of the backscattered light signal 220 with respect to the continuous wave light signal 215, i.e., the emitted light from the Brillouin light source 110A. For example, the backscattered light signal 220 detected by the light sensor 110B may be compared to known characteristics of the light emitted by the Brillouin light source 110A. In some embodiments, the determined frequency shift may then be used to characterize or calculate the acoustic signal induced by the photoacoustic light source 105 via the photoacoustic effect. The total number of Brillouin scattered light events is proportional to the magnitude of the interacting acoustic wave. Thus, the backscattered light signal 220 may be used as a measurement or quantification of the induced pressure, i.e., the acoustic signal, as would be apparent to a person having an ordinary level of skill in the art. In some embodiments, the calculated acoustic signal may be used to calculate the Grüneisen parameter. For example, the initial pressure wave ($P_0$) of the photoacoustic signal may be expressed as:

$$P_0 = \Gamma \mu_\alpha(\lambda) F$$

where $\Gamma$ is the Grüneisen parameter, $\mu_\alpha$ is the absorption coefficient for a particular wavelength $\lambda$ of emitted light, and F is the fluence. Thus, where the absorption coefficient and the fluence of the light emitted by the photoacoustic light source 105 are known, the value of the Grüneisen parameter or one of its constituent components may be calculated based on the acoustic signal. In some embodiments, the absorption coefficient may be approximated or assumed based on known properties of a particular type of tissue (e.g., ocular tissue). In some embodiments, the absorption coefficient may be determined through direct measurement. In some embodiments, the fluence of the light emitted by the photoacoustic light source 105 may be approximated or assumed based on the properties and/or settings of the photoacoustic light source 105. In some embodiments, the fluence of the emitted light may be directly measured by conventional means. Accordingly, the computing device 115 may calculate the value of the Grüneisen parameter and/or one of its constituent components.

The Grüneisen parameter may be clinically significant because it is relevant to various material characteristics and may thus provide insight related to the biomechanical properties of the target tissue 10, which may indicate a specific characteristic, state, condition, and/or disease in the target tissue. In some embodiments, the Grüneisen parameter may be calculated at various points throughout a target tissue 10 in order to define the biomechanical properties at different points or regions of the target tissue 10. For example, the Grüneisen parameter may be mapped at specific locations across the target tissue 10. In another example, the Grüneisen parameter may be mapped across an entire region of the target tissue 10 and/or a substantial entirety of the target tissue 10. In some embodiments, one or more additional biomechanical properties of the target tissue 10 may be calculated by the computing device 115 based on the Grüneisen parameter.

In some embodiments, the system may further comprise a display configured to receive the calculated Grüneisen parameter from the computing device 115 and display the Grüneisen parameter to a user. In some embodiments, additional or alternative values, characteristics, and/or information as described herein may be displayed on the display by the computing device 115.

Figure 3:
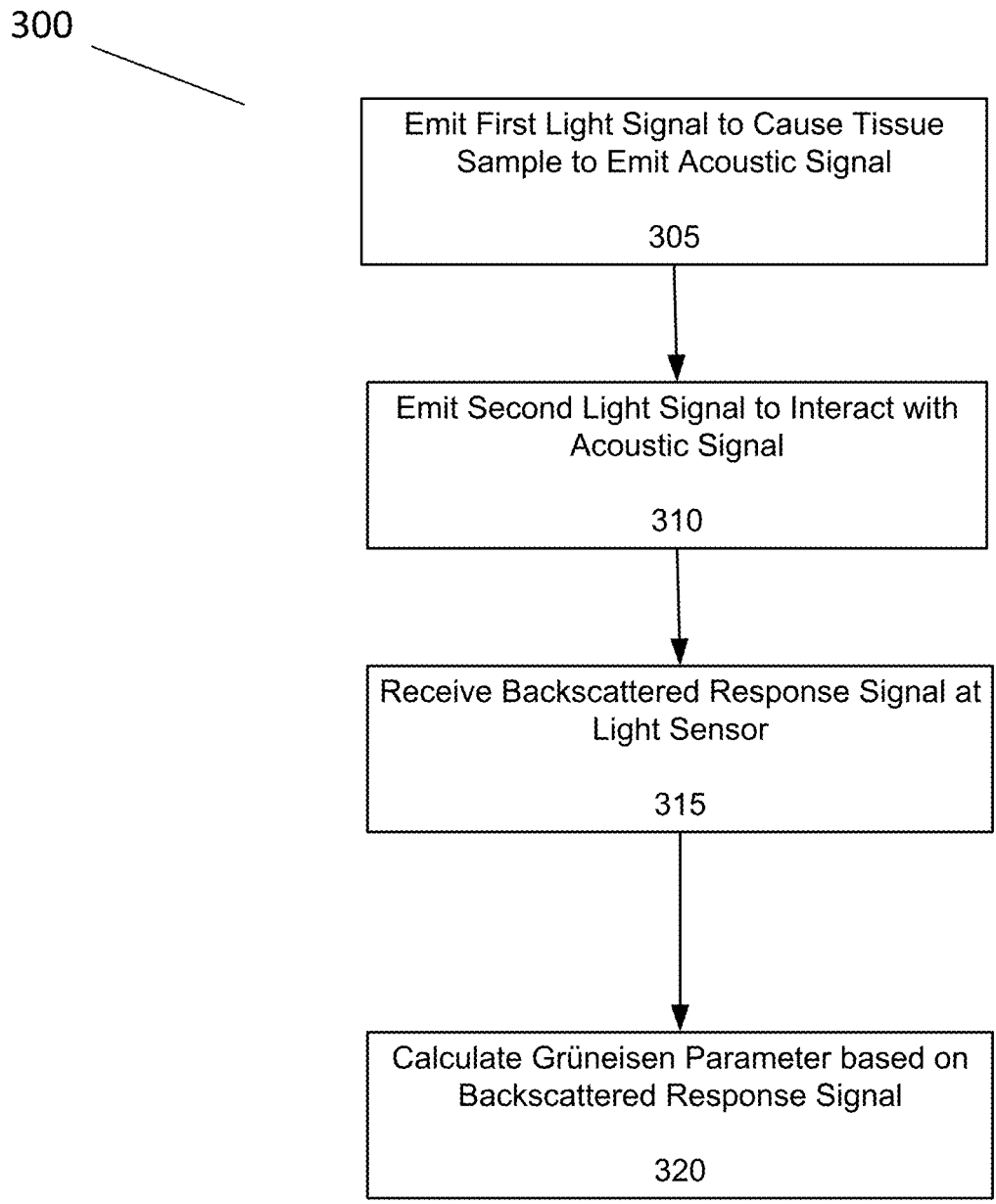
FIG. 3 depicts a flow diagram of an illustrative method of calculating the Grüneisen parameter for a tissue sample in accordance with an embodiment.

In another aspect of the present subject matter, a method of calculating a Grüneisen parameter for a tissue sample is disclosed. Referring to FIG. 3, a flow diagram of an illustrative method of calculating the Grüneisen parameter for a tissue sample is depicted in accordance with an embodiment. The method 300 comprises emitting 305 a first light signal to the tissue sample to cause the tissue sample to emit an acoustic signal and emitting 310 a second light signal to the tissue sample, wherein the second light signal is configured to interact with the acoustic signal to generate a backscattered light signal (i.e., a response signal). The method 300 further comprises receiving 315 the backscattered response signal by a light sensor and calculating 320 the Grüneisen parameter for the tissue sample based on the backscattered response signal. In some embodiments, the method 300 may be carried out utilizing the system 100.

In some embodiments, the first light signal may be configured to be absorbed by the tissue sample or a portion thereof. In some embodiments, absorption of the first light signal may induce the tissue sample to emit an acoustic signal in response to the first light signal via the photoacoustic effect. In some embodiments, the first light signal may be a pulsed light signal. For example, the first light signal may be light emitted from a photoacoustic light source 105 as fully described herein. The first light signal may comprise any characteristics and/or features as described with respect to light from the photoacoustic light source 105.

In some embodiments, the second light signal may be configured to interact with the acoustic signal according to the principles of Brillouin scattering. For example, the second light signal may undergo a Doppler frequency shift due to refraction of the second light signal caused by the acoustic signal. In some embodiments, the second light signal may be a continuous wave light signal. For example, the second light signal may be light emitted from a Brillouin light source 110A as fully described herein. The second light signal may comprise any characteristics and/or features as described with respect to light from the Brillouin light source 110A.

In some embodiments, the light sensor may be configured to detect a frequency of the backscattered light signal. In some embodiments, the light sensor comprises a high-resolution, two-stage VIPA spectrometer. In some embodiments, the light sensor may comprise a Brillouin spectrometer or a portion thereof. However, additional or alternative types of light sensors configured to detect at least one characteristic of the backscattered response signal are contemplated herein. For example, the light sensor may comprise a sensor configured to detect a characteristic from which the frequency of the backscattered response signal may be determined.

In some embodiments, calculating 320 the Grüneisen parameter comprises receiving the backscattered response signal from the light sensor and calculating a frequency shift between the second light signal and the backscattered response signal. In some embodiments, calculating 320 the Grüneisen parameter further comprises calculating a magnitude of the acoustic signal based on the frequency shift. In some embodiments, the Grüneisen parameter is calculated 320 based on the magnitude of the acoustic signal. Furthermore, the calculations may comprise any of the various calculations described herein with respect to the computing device 115 of the system 100.

In some embodiments, one or more steps of the method 300 may be performed by a processor (e.g., a computing device 115 of FIG. 1). In some embodiments, the step of calculating 320 the Grüneisen parameter may be performed by the processor. Furthermore, in some embodiments, the processor may control additional components as described herein to cause the first light signal and/or the second light signal to be emitted.

In some embodiments, the method 300 is used to calculate the Grüneisen parameter at a single point of the tissue sample. In some embodiments, the method 300 may be repeated at a plurality of points of the tissue sample to calculate the Grüneisen parameter at each of the plurality of points of the tissue sample and/or across a region of the tissue sample. For example, for a given tissue sample, the method 300 may be performed to spatially map the Grüneisen parameter and reconstruct an image representative of the Grüneisen parameter and/or related biomechanical properties derived therefrom.

In some embodiments, the method further comprises displaying the calculated Grüneisen parameter on a display. For example, the calculated Grüneisen parameter may be transmitted to a display (e.g., by the processor) and displayed to a user. In some embodiments, additional information may be displayed on the display. In some embodiments, where a plurality of measurements have been collected, the measurements may be displayed in an aggregate form, such as a chart, graphic, table, profile, or other format. For example, a spatial map or other representation of a plurality of measurements or calculations may be displayed to the user via the display. In some embodiments, the processor and/or the display may be used to monitor the Grüneisen parameter or other biomechanical properties in real time. For example, the system may be used to repeatedly collect measurements over a period of time and may be displayed and updated in real time. In some embodiments, a stimulus may be applied to the tissue sample or another test may be performed during collection of measurements in order to record a response. For example, a change in the Grüneisen parameter or another related characteristic of the tissue sample before and after the application of the stimulus may be relevant, e.g., indicating an effect of the stimulus on the tissue. In some embodiments, a drug, a biologic, or a chemopharmaceutical may be applied to the tissue sample in order to record an effect of the drug, biologic, or chemopharmaceutical on the behavior of the tissue. For example, the applied substance may have an effect on a characteristic of neurons in the tissue sample (e.g., firing patterns) that may be relevant to research and/or clinical applications.

In some embodiments, the tissue sample comprises a tissue of a patient or subject. For example, the tissue sample may comprise ocular tissue of a patient. However, it is contemplated that a variety of tissues may be assessed by the method 300. Furthermore, in some embodiments, the tissue sample comprises an in vitro sample, e.g., a biopsy. The method 300 may be used for evaluation and/or diagnosis of the patient in a clinical setting. In some embodiments, the method 300 may be used in research applications to study tissue mechanisms, diseases and/or disorders.

Figure 4:
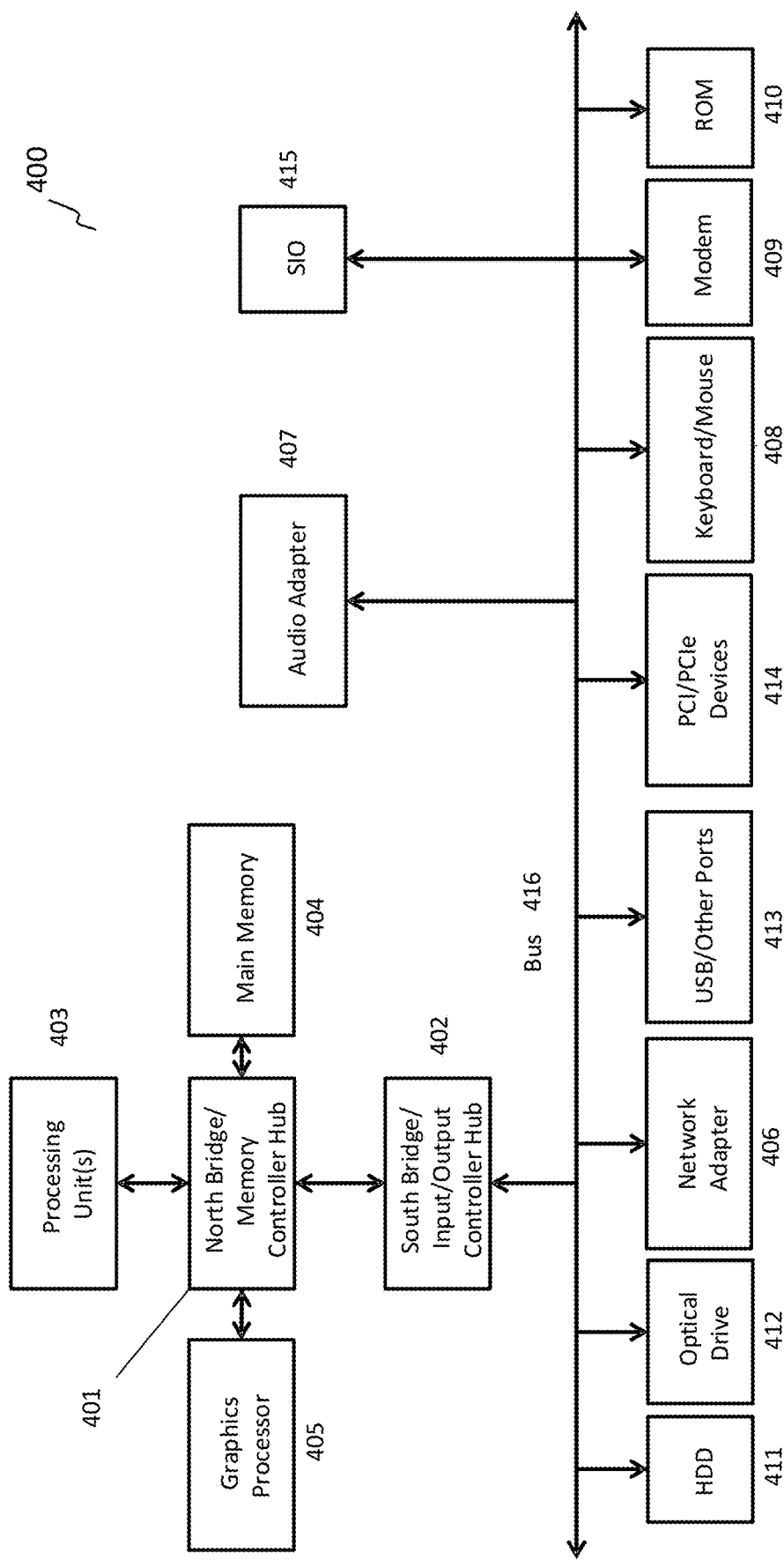
FIG. 4 illustrates a block diagram of an illustrative data processing system in which aspects of the illustrative embodiments are implemented.

FIG. 4 illustrates a block diagram of an illustrative data processing system 400 in which aspects of the illustrative embodiments are implemented. The data processing system 400 is an example of a computer, such as a server or client, in which computer usable code or instructions implementing the process for illustrative embodiments of the present technology are located. In some embodiments, the data processing system 400 may be a server computing device. For example, data processing system 400 can be implemented in a server or another similar computing device. The data processing system 400 can be configured to, for example, transmit and receive information related to the light signals, photoacoustic signal and/or Grüneisen parameter.

In the depicted example, data processing system 400 can employ a hub architecture including a north bridge and memory controller hub (NB/MCH) 401 and south bridge and input/output (I/O) controller hub (SB/ICH) 402. Processing unit 403, main memory 404, and graphics processor 405 can be connected to the NB/MCH 401. Graphics processor 405 can be connected to the NB/MCH 401 through, for example, an accelerated graphics port (AGP).

In the depicted example, a network adapter 406 connects to the SB/ICH 402. An audio adapter 407, keyboard and mouse adapter 408, modem 409, read only memory (ROM) 410, hard disk drive (HDD) 411, optical drive (e.g., CD or DVD) 412, universal serial bus (USB) ports and other communication ports 413, and PCI/PCIe devices 414 may connect to the SB/ICH 402 through bus system 416. PCI/PCIe devices 414 may include Ethernet adapters, add-in cards, and PC cards for notebook computers. ROM 410 may be, for example, a flash basic input/output system (BIOS). The HDD 411 and optical drive 412 can use an integrated drive electronics (IDE) or serial advanced technology attachment (SATA) interface. A super I/O (SIO) device 415 can be connected to the SB/ICH 402.

An operating system can run on the processing unit 403. The operating system can coordinate and provide control of various components within the data processing system 400. As a client, the operating system can be a commercially available operating system. An object-oriented programming system, such as the Java™ programming system, may run in conjunction with the operating system and provide calls to the operating system from the object-oriented programs or applications executing on the data processing system 400. As a server, the data processing system 400 can be an IBM® eServer™ System® running the Advanced Interactive Executive operating system or the Linux operating system. The data processing system 400 can be a symmetric multiprocessor (SMP) system that can include a plurality of processors in the processing unit 403. Alternatively, a single processor system may be employed.

Instructions for the operating system, the object-oriented programming system, and applications or programs are located on storage devices, such as the HDD 411, and are loaded into the main memory 404 for execution by the processing unit 403. The processes for embodiments described herein can be performed by the processing unit 403 using computer usable program code, which can be located in a memory such as, for example, main memory 404, ROM 410, or in one or more peripheral devices.

A bus system 416 can be comprised of one or more busses. The bus system 416 can be implemented using any type of communication fabric or architecture that can provide for a transfer of data between different components or devices attached to the fabric or architecture. A communication unit such as the modem 409 or the network adapter 406 can include one or more devices that can be used to transmit and receive data.

Those of ordinary skill in the art will appreciate that the hardware depicted in FIG. 4 may vary depending on the implementation. Other internal hardware or peripheral devices, such as flash memory, equivalent non-volatile memory, or optical disk drives may be used in addition to or in place of the hardware depicted. Moreover, the data processing system 400 can take the form of any of a number of different data processing systems, including but not limited to, client computing devices, server computing devices, tablet computers, laptop computers, telephone or other communication devices, personal digital assistants, and the like. Essentially, data processing system 400 can be any known or later developed data processing system without architectural limitation.

Although the present invention has been described in considerable detail with reference to certain preferred embodiments thereof, other versions are possible. Therefore the spirit and scope of the appended claims should not be limited to the description and the preferred versions contained within this specification. Various aspects of the present invention will be illustrated with reference to the following non-limiting examples:

EXAMPLES

Example 1—Measurement of Grüneisen Parameter Via Photoacoustic Effect and Brillouin Spectroscopy Brillouin spectroscopy is hypothesized to allow for accurate detection of the photoacoustic effect. Experiments will investigate an integrated multimodal optical system for its ability to quantify the photoacoustic effect and the constituent parameters. This will allow for extraction of the biomechanical properties of cells and tissues by way of measuring the Grüneisen Parameter using Brillouin spectroscopy. These systems will be investigated for in vitro and in vivo applications.

Example 1.1—Optical System for Combined Photoacoustic Wave Generation and Point Sampling in Brillouin Spectroscopy Methods. An integrated system will implement principles of concentrically generating and detecting the photoacoustic effect in combination state-of-the-art Brillouin spectroscopy systems. The concentric illumination of a pulsed laser (used for photoacoustic generation) and a continuous wave laser (used for Brillouin scattering), as shown in FIG. 2A, can be achieved through several configurations. Where the pulsed laser and the continuous wave laser are different wavelengths, excitation and emission filters along with a dichroic mirror, can be utilized in the configuration typical of most fluorescent microscopes (e.g., as shown in FIG. 1). For some applications, Brillouin scattering and photoacoustic imaging experiments may require the use of lasers of the same wavelengths. For such configurations, a series of waveplates and polarizing beam splitters can be implemented as is typically implemented in Brillouin microscopy. Regardless of the wavelengths of the pulsed and continuous wave lasers, the system may utilize a dual axis configuration where parallel beams are introduced into the same objective lens, resulting in a slight beam cross angle.

In order to account for noise in the system, different configurations will be investigated to minimize back scattering into the Brillouin spectrometer. For example, by implementing different wavelengths or polarizations for the pulsed laser and continuous wave laser, concentric light delivery may be enabled without allowing stray light into the spectrometer.

Anticipated Results. Testing of the potential system configurations and techniques described will yield an optical system with the requisite requirements to accurately detect biomechanical properties of a tissue sample with high sensitivity and fast response time.

Example 1.2—Measuring, Validating, and Characterizing Mechanical Properties of Biological Tissues Methods. Brillouin spectroscopy is able to detect relatively weak spontaneous pressure waves that are naturally occurring in tissue. Accordingly, this technique may be very sensitive to stronger acoustic waves. For example, previous experiments have used ultrasound waves optically generated from thin metal films to induce Brillouin scattering. Accordingly, Brillouin spectroscopy will be tested in response to the stronger acoustic waves generated by the photoacoustic effect to determine the level of sensitivity. In application, the total number of Brillouin scattered light events is expected to be proportional to the magnitude of the interacting acoustic wave. Accordingly, this measurement may provide quantification of the induced pressure wave for calculation of the Grüneisen Parameter.

Anticipated Results. It is anticipated that Brillouin spectroscopy will yield measurements of stronger acoustic waves such as photoacoustic signals with high sensitivity. Furthermore, the calculation of the photoacoustic waves by this technique will provide an accurate quantification of the induced photoacoustic waves, thereby enabling calculation of the Grüneisen Parameter in a contactless and contrast-free manner to a degree of accuracy equal to or greater than conventional systems.

Example 2—Development of Dual Brillouin/Photoacoustic Microscopy (B-PAM) for Direct Measurement of Grüneisen Parameter While the conventional method for acoustic detection in traditional PAM architectures utilize transducers and/or a coupling medium to allow the signal to travel with little attenuation. However, contactless detection may improve the applicability of such techniques to clinical applications.

Example 2.1—Development of B-PAM System

Methods. In order to obtain a B-PAM system with sufficient resolution for clinical applications, optical configurations will be explored for concentric and overlapping submicron diffraction limited excitation and detection of the photoacoustic effect. Using photoacoustic contrast agents, such as gold nanoparticles, the pointspread-function (PSF) of the B-PAM system in several locations throughout the imaging window will be quantified. For in vivo applications, the detection and excitation beams will be raster scanned, allowing for the possibility of non-concentric illumination, thus broadening the PSF and decreasing the sensitivity of the system.

Anticipated Results. A B-PAM system with overlapping and concentric sub-micron diffraction limited spots will provide sufficient resolution for estimation of the photoacoustic wave. High repetition pulsed rate lasers (greater than about 1 kHz) will provide relatively quick scan times as compared to conventional systems.

Example 2.2—Reconstructing Images Representative of Biomechanical Properties of Tissue Methods. With proper estimations of the photoacoustic effect, it is theorized that approximation of the Grüneisen Parameter is possible. Calculations require knowledge or measurement of not only the photoacoustic wave, but also fluence and absorption coefficients. A sufficiently accurate system will enable the calculation of the Grüneisen Parameter, or the constituent parameters, for specific spatial locations across the sample. This will enable mapping of the Grüneisen Parameter across the sample, e.g., for clinical evaluation and/or diagnosis.

Anticipated Results. Calculation of the Grüneisen Parameter based on estimated photoacoustic waves will provide sufficient accuracy for use in a clinical setting and allow mapping of biomechanical characteristics of a tissue at different spatial locations with high resolution as compared to conventional techniques.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Instead, this application is intended to cover any variations, uses, or adaptations of the present teachings and use its general principles. Further, this application is intended to cover such departures from the present disclosure as come within known or customary practice in the art to which these teachings pertain. Many modifications and variations can be made to the particular embodiments described without departing from the spirit and scope of the present disclosure as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A contactless system for calculating a Grüneisen parameter of a live target tissue, the system comprising:
   a first light source configured to emit a first light signal to the target tissue, wherein the first light signal is configured to generate an acoustic signal in the target tissue;
   wherein the first light source is a nanosecond pulsed laser, a neodymium doped yttrium aluminum garnet (Nd:YAG) laser, a titanium-sapphire laser, or a continuous wave laser;
   a second light source configured to emit a second light signal to the target tissue, wherein interaction of the second light signal with the acoustic signal causes backscattering of the second light signal to generate a backscattered light signal;
   wherein the second light source has a wavelength of about 780 nm;
   wherein the first light source and the second light source are housed in an optical enclosure;
   wherein the optical enclosure further comprises a light sensor, a collimating lens, a dichroic mirror, and a motorized objective lens;
   wherein the light sensor is configured to detect the backscattered light signal;
   wherein the motorized objective lens is configured to be positioned at a distance from the target tissue such that there is an air gap between the motorized objective lens and the target tissue, configured to focus the first and second light sources onto the target tissue;
   wherein the first light source and the second light source are configured to concentrically emit the first light signal and the second light signal through the air gap to the target tissue;
   wherein the backscattered light signal is transmitted to the light sensor through the air gap, the motorized objective lens and the dichroic mirror;
   a processor; and
   a non-transitory, computer-readable medium storing instructions that, when executed, cause the processor to:
   activate the first light source;
   activate the second light source;
   receive one or more electrical signals indicative of the backscattered light signal from the light sensor;
   determine a frequency shift of the backscattered light signal with respect to the second light signal;
   calculate a magnitude of the acoustic signal based on the frequency shift;
   calculate, based on the backscattered light signal and a magnitude of the acoustic signal based on the frequency shift, the Grüneisen parameter of the target tissue; and
   display the calculated Grüneisen parameter.

2. The system of claim 1, wherein the first light signal has a frequency of 1 kHz or greater.

3. The system of claim 1, wherein the first light signal comprises one of an ultraviolet light signal, a visible light signal, and a near infrared light signal.

4. The system of claim 1, wherein the second light source comprises a continuous wave laser.

5. The system of claim 1, wherein the optical enclosure comprises a Brillouin spectrometer comprising the second light source and the light sensor.

6. The system of claim 1, wherein the first light signal is configured to induce photoacoustic effects in the target tissue, thereby causing the generation of the acoustic signal.

7. The system of claim 6, wherein the first light signal is configured to be absorbed by one or more subcellular components of the target tissue, thereby resulting in the photoacoustic effects.

8. The system of claim 7, wherein the one or more subcellular components comprise one or more of DNA, RNA, cytoplasm, and a myelin sheath.

9. The system of claim 1, wherein a frequency of the backscattered light signal is different from a known frequency of the second light signal.

10. The system of claim 1, wherein the instructions that cause the processor to calculate the Grüneisen parameter comprise instructions that, when, executed cause the processor to calculate the Grüneisen parameter further based on a fluence of the first light signal and an absorption coefficient of the target tissue.

11. The system of claim 1, wherein the instructions, when executed, further cause the processor to:
   receive, for each of a plurality of locations of the target tissue, one or more electrical signals indicative of the backscattered light signal associated with each of the plurality of locations; and
   calculate, based on the backscattered light signal, the Grüneisen parameter of the target tissue for each of the plurality of locations.

12. The system of claim 11, wherein the instructions, when executed, further cause the processor to construct a spatial map of the Grüneisen parameter across the plurality of locations of the target tissue.

* * * * *